United States Patent [19]

Seghizzi et al.

[11] Patent Number: 5,443,842
[45] Date of Patent: Aug. 22, 1995

[54] ORAL FORMULATIONS OF UBIDECARENONE IN FORM OF CAPSULES

[75] Inventors: Roberto Seghizzi; Giuseppe Furiosi, both of Milan, Italy

[73] Assignee: Inverni Della Beffa Farmaceutici S.r.l., Milan, Italy

[21] Appl. No.: 220,258

[22] Filed: Mar. 30, 1994

[30] Foreign Application Priority Data

Mar. 30, 1993 [IT] Italy .................. MI93A0605

[51] Int. Cl.⁶ .................................. A61K 9/48
[52] U.S. Cl. ........................ 424/456; 424/455; 424/94.1
[58] Field of Search ............... 424/455, 456, 94.1

[56] References Cited

U.S. PATENT DOCUMENTS

| | | | |
|---|---|---|---|
| 4,869,900 | 9/1989 | Pozzi et al. | 424/94.1 |
| 4,944,949 | 7/1990 | Story et al. | 424/455 |
| 5,037,698 | 8/1991 | Brunel | 424/455 |
| 5,110,602 | 5/1992 | Kim et al. | 424/451 |
| 5,139,740 | 8/1992 | Uesugi et al. | 424/455 |
| 5,140,021 | 8/1992 | Maxson et al. | 424/455 |
| 5,153,001 | 10/1992 | Ismail | 424/455 |
| 5,200,192 | 4/1993 | Wimmer | 424/455 |
| 5,206,219 | 4/1993 | Desai | 424/455 |

FOREIGN PATENT DOCUMENTS 522433  1/1993  European Pat. Off. .
081813  6/1980  Japan .

*Primary Examiner*—Melvyn I. Marquis
*Assistant Examiner*—Amy Hulina
*Attorney, Agent, or Firm*—Bucknam and Archer

[57] ABSTRACT

Pharmaceuticals formulations are described, in form of capsules ad oral use, containing as the active ingredient ubidecarenone, characterized in that the active ingredient is dispersed in a mixture of isopropyl myristate or isopropyl palmitate with polyethoxylated, hydrogenated or non hydrogenated, castor oils.

5 Claims, No Drawings

ORAL FORMULATIONS OF UBIDECARENONE IN FORM OF CAPSULES

The present invention relates to pharmaceuticals formulations, in form of capsules for oral use, containing as the active ingredient ubidecarenone.

Ubidecarenone, or coenzyme Q10, is a physiological element present in the cells as a component of the mitochondrial respiratory chain (De Pierre V. C. et al., Ann. Rev. Biochem., 46, 201, 1977; Nakamura T. et al., Chem. Pharm. Bull. 27, 1101, 1979). Ubidecarenone acts directly on the oxidative phosphorylation processes for the production of energy (formation of ATP) through metabolic, especially aerobic, pathways.

The ubidecarenone requirements can increase in normal subjects who are subjected to intense physical fatigue or in subjects suffering from cardiovascular disorders, chronic debilitating diseases or subjected to chronic pharmacological treatments. Particularly, a lack in ubidecarenone has been evidenced in ischaemic cardiopathy, in senile miocardiosclerosis and in hypertensive cardiopathy (Yamagami T. et al., Biomedical and Clinical Aspects of Coenzyme Q10, Elsevier/North-Holland Biomedical Press Vol. 3, 79, 1981; Kishi T. et al., ibidem Vol. 3, 67). In such pathologies, the supply of exogenous ubidecarenone involves remarkable improvements as well as important therapeutical results (Yamasawa G., Biomedical and Clinical Aspects of Coenzime Q10, Elsevier/North-Holland Biomedical Press Vol. 2, 333, 1980).

Ubidecarenone is a lipophilic, low melting solid, practically insoluble in water. Such characteristics restrict its capability of dissolution in gastrointestinal fluids, when it is administered in conventional formulations containing it in solid form (tablets, capsules, suspensions for reconstitution before use).

Italian Patent Application N° 001919 A/91 describes preparations in form of aqueous solutions for oral use containing ubidecarenone dissolved by means of hydrogenated polyethoxylated 40 castor oil, a non-ionic surfactant compatible with oral use. The dissolution of ubidecarenone allows to attain blood levels of the active ingredient higher and more protracted than those obtained with a conventional preparation in suspension for reconstitution before use.

Japanese Patent 55081813 discloses preparations in soft capsules containing ubidecarenone dissolved in a mixture of neutral oils with surfactants. The following neutral oils are cited: soy-bean oil, peanut oil, cottonseed oil, cod-liver oil, fatty acids triglycerides; a number of different surfactants are described, particularly, hydrogenated polyethoxylated castor oil.

However, formulations in gelatin capsules prepared using one of said neutral oils (peanut oil) and hydrogenated polyethoxylated castor oil as the surfactant, in weight ratios ranging from those cited in JP 55081813, release ubidecarenone in dissolved form only in minimal amounts, when subjected to the water dissolution test.

Preparations comprising, besides ubidecarenone, only either a neutral oil or a surfactant, have a similar behaviour.

It has surprisingly been found, and it is the object of the present invention, that solid oral formulations, containing ubidecarenone dispersed in a mixture of isopropyl myristate or isopropyl palmitate with polyethoxylated castor oils, are capable of releasing the active ingredient in dissolved form when contacted with an aqueous medium. Therefore, such formulations allow to obtain increases in bioavailability compared with the conventional oral solid forms.

The oily carrier, preferably isopropyl myristate, having the role of solubilizer of ubidecarenone, is present in amounts ranging from 1 to 5 times the weight of the active ingredient, preferably twice the weight.

The surfactant, acting as a solubilizer of the oily phase in water (ubidecarenone +oily carrier), belongs to the class of polyethoxylated, hydrogenated or non hydrogenated, castor oils, and it is preferably hydrogenated polyethoxylated 40 castor oil. The surfactant is present in amounts ranging from 1 to 5 times the weight of the active ingredient, preferably 3 times the weight.

A main object of the present invention is that the oily phase (ubidecarenone+oily carrier): surfactant ratio must range from 1:0.3 to 1:2.5, preferably 1:1.

The formulation is prepared dissolving ubidecarenone in the oil/surfactant mixture, at a temperature of 50° C. After cooling to room temperature, the formulation is placed into gelatin capsules.

A further main object of the present invention is that the disclosed formulations, although being semisolid suspensions at room temperature, become fluid oily solutions at the body temperature, releasing ubidecarenone in dissolved form when subjected to the dissolution test in water.

The following examples illustrate the invention in greater detail.

EXAMPLE 1

Gelatin Capsules Containing 50 mg of Ubidecarenone

One capsule contains:

| | |
|---|---|
| Ubidecarenone | 50 mg |
| Hydrogenated polyethoxylated 40 castor oil | 150 mg |
| Isopropyl myristate | 100 mg |

The mixture of 150 g of hydrogenated polyethoxylated 40 castor oil and 100 g of isopropyl myristate is heated to 50° C., under continuous stirring, until a clear liquid is obtained. 50 g of ubidecarenone are added, stirring until complete dissolution of the active ingredient. After cooling to room temperature, under continuous stirring, the formulation is filled into capsules, dosing 300 mg/capsule.

EXAMPLE 2

Gelatin Capsules Containing 50 Mg of Ubidecarenone

One capsule contains:

| | |
|---|---|
| Ubidecarenone | 50 mg |
| Hydrogenated polyethoxylated 40 castor oil | 50 mg |
| Isopropyl myristate | 50 mg |

The preparation was carried out according to the procedure described in example 1.

EXAMPLE 3

Gelatin Capsules Containing 50 mg of Ubidecarenone

One capsule contains:

| | |
|---|---|
| Ubidecarenone | 50 mg |
| Hydrogenated polyethoxylated 40 castor oil | 250 mg |

| | |
|---|---|
| Isopropyl myristate | 50 mg |

The preparation was carried out according to the procedure described in example 1.

EXAMPLE 4

Gelatin Capsules Containing 50 mg of Ubidecarenone

One capsule contains:

| | |
|---|---|
| Ubidecarenone | 50 mg |
| Polyethoxylated 35 castor oil | 150 mg |
| Isopropyl myristate | 100 mg |

The preparation was carried out according to the procedure described in example 1.

EXAMPLE 5

Gelatin Capsules Containing 50 mg of Ubidecarenone

One capsule contains:

| | |
|---|---|
| Ubidecarenone | 50 mg |
| Hydrogenated polyethoxylated 40 castor oil | 150 mg |
| Peanut oil | 100 mg |

The preparation was carried out according to the procedure described in example 1.

EXAMPLE 6 (corresponding to a formulation in weight ratios as described in JP 55081813)

Gelatin Capsules Containing 50 mg of Ubidecarenone

One capsule contains:

| | |
|---|---|
| Ubidecarenone | 50 mg |
| Hydrogenated polyethoxylated 40 castor oil | 100 mg |
| Peanut oil | 500 mg |

The preparation was carried out according to the procedure described in example 1.

EXAMPLE 7

Gelatin Capsules Containing 50 mg of Ubidecarenone

One capsule contains:

| | |
|---|---|
| Ubidecarenone | 50 mg |
| Hydrogenated polyethoxylated 40 castor oil | 150 mg |

The preparation was carried out according to the procedure described in example 1.

EXAMPLE 8 (corresponding to a commercial formulation of ubidecarenone 50 mg, tablets)

One tablet contains:

| | |
|---|---|
| Ubidecarenone | 50 mg |
| Maize starch | 60 mg |
| Lactose | 15 mg |
| Methyl cellulose | 2 mg |
| Microgranular cellulose | 77 mg |
| Precipitated silica | 13 mg |
| Magnesium stearate | 3 mg |
| Sodium carboxymethyl cellulose | 15 mg |

| | |
|---|---|
| Talc | 10 mg |

EXAMPLE 9 (corresponding to a commercial formulation of ubidecarenone 50 mg, capsules)

One capsule contains:

| | |
|---|---|
| Ubidecarenone | 50 mg |
| Lactose | 130 mg |
| Precipitated silica | 10 mg |
| Sodium lauryl sulfate | 5 mg |
| Magnesium stearate | 5 mg |

The release characteristics of the formulations described in examples 1–9 were evaluated by means of the dissolution test with devices according to Ph. Eur. 2°, fitted with a paddle stirrer at a speed of 75 rotations/min. Depurated water was used as the dissolution medium.

The results from the dissolution tests, expressed in Table 1 as the percentage of dissolved ubidecarenone compared with the nominal content of the capsules, evidenced that:

the formulations in capsules of the invention provide the dissolution of ubidecarenone in an aqueous medium, contrary to the commercial oral solid formulations (examples 1–4 vs. 8,9);

ubidecarenone can be dissolved in an aqueous medium when in formulation, besides the surfactant (polyethoxylated, hydrogenated or non hydrogenated castor oil), isopropyl myristate or palmitate (examples 1–4 vs. 7) is present. Such an object cannot be obtained with other oily carriers, such as peanut oil, soy-bean oil (examples 1–4 vs. 5,6).

The preparations obtained with the compositions of the invention, even though in form of semisolid suspensions at room temperature, become fluid oily solutions at the body temperature, allowing ubidecarenone to be dissolved in an aqueous medium and therefore increasing its bioavailability.

TABLE 1

| Time minutes | Dissolved ubidecarenone (%) | | | | | | | | |
|---|---|---|---|---|---|---|---|---|---|
| | Ex. 1 | Ex. 2 | Ex. 3 | Ex. 4 | Ex. 5 | Ex. 6 | Ex. 7 | Ex. 8 | Ex. 9 |
| 15 | 29 | 9 | 12 | 30 | — | — | — | — | — |
| 30 | 86 | 41 | 35 | 80 | 5 | 3 | 4 | 1 | 2 |
| 45 | 100 | 54 | 47 | 90 | — | — | — | — | — |
| 60 | 101 | 82 | 65 | 94 | 15 | 7 | 10 | 3 | 3 |

The profiles of the dissolution tests of the formulations described in examples 1–4, which are not intended to limit the invention, confirm that ubidecarenone oral solid formulations can be obtained, which are capable of releasing the active ingredient in a dissolved form in an aqueous medium.

The formulations of the invention comprise both hard and soft gelatin capsules, containing ubidecarenone in amounts ranging from 5 to 100 mg, preferably from 20 to 60 mg.

We claim:

1. A pharmaceutical formulation for oral use, comprising a capsule containing as the active ingredient ubidecarenone dispersed in a mixture of a) isopropyl myristate or isopropyl palmitate and b) polyethoxylated, hydrogenated or non-hydrogenated castor oils, wherein said isopropyl myristate or isopropyl palmitate is in an amount of 1–5 times the weight of said ubidecarenone and said polyethoxylated hydrogenated or non-hydrogenated castor oils are in an amount of 1–5 times the weight of said ubidecarenone and the ratio of ubidecarenone and said isopropyl myristate or isopropyl palmitate to said polyethoxylated castor oils ranges from 1:0.3 to 1:2.5.

2. The formulation according to claim 1 wherein said ubidecarenone is in an amount of 5–100 mgs. per capsule or tablet.

3. The formulation according to claim 1 wherein said isopropyl myristate or isopropyl palmitate is in an amount of twice the weight of said ubidecarenone and the weight of said polyethoxylated castor oils is in an amount of three times the weight of said ubidecarenone.

4. A process for the preparation of a formulation for oral use which contains ubidecarenone as the active ingredient which comprises dissolving ubidecarenone in a mixture of isopropyl myristate or isopropyl palmitate and polyethoxylated, hydrogenated or non-hydrogenated castor oils, the amount of said isopropyl myristate or isopropyl palmitate being 1–5 times the weight of said ubidecarenone and the amount of said polyethoxylated hydrogenated or non-hydrogenated castor oils being 1–5 times the weight of said ubidecarenone and the ratio of ubidecarenone and said isopropyl myristate or isopropyl palmitate to said polyethoxylated castor oils ranges from 1:0.3 to 1:2.5 , said mixture being previously heated to 50° C., until a clear liquid is obtained, then cooling to room temperature and finally placing said clear liquid into capsules.

5. A method of treatment of a human subject in need of ubidecarenone which consists of administering orally to said subject a pharmaceutical formulation in the form of capsules, each capsule containing as the active ingredient 5–100 mgs of ubidecarenone dispersed in a mixture of a) isopropyl myristate or isopropyl palmitate and b) polyethoxylated, hydrogenated or non-hydrogenated castor oils, wherein said isopropyl myristate or isopropyl palmitate is in an amount of 1–5 times the weight of said ubidecarenone and said polyethoxylated hydrogenated or non-hydrogenated castor oils are in an amount of 1–5 times the weight of said ubidecarenone and the ratio of ubidecarenone and said isopropyl myristate or isopropyl palmitate to said polyethoxylated castor oils ranges from 1:0.3 to 1:2.5.

* * * * *